(12) United States Patent
Marat et al.

(10) Patent No.: US 11,389,385 B2
(45) Date of Patent: Jul. 19, 2022

(54) RESORCINOL DERIVATIVES FOR THEIR COSMETIC USE

(71) Applicant: L'OREAL, Paris (FR)

(72) Inventors: Xavier Marat, Aulnay-sous-Bois (FR); Chunyu Ma, Shanghai (CN)

(73) Assignee: L'OREAL, Paris (FR)

( * ) Notice: Subject to any disclaimer, the term of this patent is extended or adjusted under 35 U.S.C. 154(b) by 123 days.

(21) Appl. No.: 16/650,645

(22) PCT Filed: Sep. 27, 2018

(86) PCT No.: PCT/EP2018/076308
§ 371 (c)(1),
(2) Date: Mar. 25, 2020

(87) PCT Pub. No.: WO2019/063710
PCT Pub. Date: Apr. 4, 2019

(65) Prior Publication Data
US 2020/0246240 A1    Aug. 6, 2020

(30) Foreign Application Priority Data
Sep. 29, 2017   (FR) ...................................... 17 59069

(51) Int. Cl.
| | | |
|---|---|---|
| *A61K 8/49* | (2006.01) |
| *A61K 45/06* | (2006.01) |
| *A61Q 19/02* | (2006.01) |
| *C07D 233/64* | (2006.01) |
| *C07D 235/12* | (2006.01) |
| *C07D 263/32* | (2006.01) |
| *C07D 263/57* | (2006.01) |
| *C07D 277/24* | (2006.01) |
| *C07D 277/64* | (2006.01) |

(52) U.S. Cl.
CPC ............ *A61K 8/4946* (2013.01); *A61K 8/494* (2013.01); *A61K 45/06* (2013.01); *A61Q 19/02* (2013.01); *C07D 233/64* (2013.01); *C07D 235/12* (2013.01); *C07D 263/32* (2013.01); *C07D 263/57* (2013.01); *C07D 277/24* (2013.01); *C07D 277/64* (2013.01)

(58) Field of Classification Search
None
See application file for complete search history.

(56) References Cited

U.S. PATENT DOCUMENTS

| | | |
|---|---|---|
| 2010/0016347 A1 | 1/2010 | Nandy et al. |
| 2013/0209383 A1 | 8/2013 | Nandy et al. |
| 2014/0050683 A1 | 2/2014 | Poigny et al. |
| 2014/0363388 A1 | 12/2014 | Nandy et al. |
| 2016/0083322 A1 | 3/2016 | Nandy et al. |
| 2017/0275224 A1 | 9/2017 | Nandy et al. |

FOREIGN PATENT DOCUMENTS

| | | |
|---|---|---|
| WO | WO 2010/011630 A1 | 1/2010 |
| WO | WO 2012/107421 A1 | 8/2012 |

OTHER PUBLICATIONS

International Search Report dated Nov. 23, 2018 in PCT/EP2018/076308 filed on Sep. 27, 2018.
Japanese Office Action dated Mar. 1, 2021 in Japanese Patent Application No. 2020-514587 (with English language summary), 6 pages.

*Primary Examiner* — Jessica Worsham
(74) *Attorney, Agent, or Firm* — Oblon, McClelland, Maier & Neustadt, L.L.P.

(57) ABSTRACT

The invention relates to resorcinol-based compounds of formula (I), to the salts, solvates, optical and/or geometrical isomers thereof, to the use thereof as active agents for depigmenting, lightening and/or bleaching keratin materials, and/or for preventing, reducing and/or treating impairment of the skin complexion or of the colour of the semi-mucous membranes. The invention also relates to a non-therapeutic cosmetic treatment process for depigmenting, lightening and/or bleaching keratin materials, and/or for preventing, reducing and/or treating impairment of the skin complexion or the colour of the semi-mucous membranes.

Formula (I)

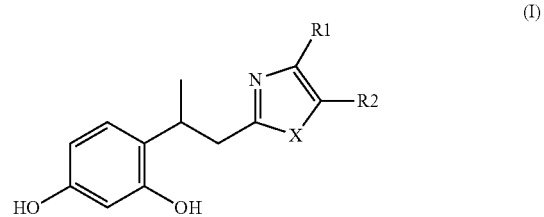

13 Claims, No Drawings

RESORCINOL DERIVATIVES FOR THEIR COSMETIC USE

The present invention relates to the field of cosmetic products, more particularly intended for caring for keratin materials, in particular caring for the skin of the face and/or of the body.

More particularly, the present invention is directed towards proposing the use of novel resorcinol-based compounds for effectively depigmenting and/or lightening, or even bleaching, keratin materials, especially the skin of the face and/or of the body and/or for improving the complexion, especially the homogeneity and radiance thereof.

The term "skin" means all of the skin of the body, including the scalp, the mucous membranes, the semi-mucous membranes, and the skin appendages. The term "skin appendages" means the bodily hair, the eyelashes, the hair and the nails. More particularly, in the present invention, the skin of the neckline, the neck and the face, the hands, the underarms and especially the skin of the face, are considered.

The colour of human skin is mainly determined by the nature and concentration of a pigment, melanin. There are two types of melanin in epidermal cells, eumalanin, which is a brown-black coloured pigment, and pheomelanin, which is a yellow-orange coloured pigment. Melanin is synthesized by specific dendritic cells, called melanocytes, located in the basal layer of the epidermis. Melanogenesis, i.e. the formation of melanin, takes place in specific organelles, the melanosomes, which, loaded with melanin, are transferred to the neighbouring epidermal cells, the keratinocytes, via the dendrites.

The mechanism of melanogenesis is particularly complex and schematically involves the following main steps:

Tyrosine→Dopa→Dopaquinone→Dopachrome→Melanin

Inside the melanosomes, three enzymes, namely tyrosinase, Tyrp 1 (for Tyrosinase-related protein 1) and Dct/Tyrp2 (for DOPAchrome tautomerase/Tyrosinase-related protein 2), play a major role in melanin production. More particularly, tyrosinase is the essential enzyme which regulates the first steps of eumelanin and pheomelanin synthesis.

The pigmentation of the skin of the face and/or of the body, and more particularly the pigmentation of the skin, depends on various factors, such as environmental factors linked to the seasons of the year, and the individual's origin.

In addition, at various periods of their life, some people see the appearance on their skin, and more especially on the hands, of darker and/or more highly coloured spots, which give the skin heterogeneity. These spots are also due to a high concentration of melanin in the skin.

A substance is acknowledged as being depigmenting if it acts directly on the vitality of the epidermal melanocytes where melanogenesis takes place, and/or if it interferes with one of the steps of melanin biosynthesis, either by inhibiting one of the enzymes involved in melanogenesis, or by inserting itself as a structural analogue of one of the chemical compounds of the melanin synthesis chain, which chain can then be blocked, thus ensuring depigmentation.

Arbutin and kojic acid are known as skin depigmenting agents.

The compound 5-[(E)-2-(4-hydroxyphenyl)ethenyl]benzene-1,3-diol, which is an aromatic resorcinol, is also known as a skin depigmenting agent, especially in JP01038009.

Substances with efficient depigmenting action, especially better than that of the compound 5-[(E)-2-(4-hydroxyphenyl)ethenyl]benzene-1,3-diol, have been sought.

Certain resorcinol-based compounds are already known in the prior art for their depigmenting activity. In this regard, mention may be made in particular of FR2971249.

There remains a need for a new agent for bleaching keratin materials, especially the skin, which also makes it possible especially to improve the homogeneity of the complexion and to revive the radiance of the complexion, the action of which is as effective as those which are known, but which does not have their drawbacks, i.e. which is stable, non-toxic to the skin and effective even at low concentration.

In this regard, the Applicant Company has, surprisingly and unexpectedly, discovered that particular active agents have good depigmenting activity and also an action which allows them to prevent, reduce and/or treat impairment of the skin complexion or of the colour of the semi-mucous membranes, i.e. in particular an activity which allows them to improve the homogeneity of the complexion and to revive the radiance of the complexion, even at low concentration.

In this regard, the Applicant has discovered, surprisingly and unexpectedly, that certain resorcinol derivatives have good depigmenting activity, even at low concentration, without showing any cytotoxicity.

One subject of the invention is thus the compounds of formula (I) as defined below.

Similarly, a subject of the invention is a composition comprising, in a physiologically acceptable medium, at least one compound of formula (I) as defined below.

The invention also relates to the non-therapeutic cosmetic use of at least one compound of formula (I) as defined below as an active agent for depigmenting, lightening and/or bleaching keratin materials, especially the skin of the face and/or of the body, and/or for preventing, reducing and/or treating impairment of the skin complexion or of the colour of the semi-mucous membranes.

The inventors have in fact demonstrated that the abovementioned compounds of formula (I) as defined in the present invention have depigmenting, lightening or even bleaching activity on keratin materials, especially on the skin. More particularly, it has been shown, as detailed in the experimental section below, that these compounds of formula (I) reduce melanin synthesis.

In particular, the present invention relates to the cosmetic use of at least one compound of formula (I) as defined in the present invention or a cosmetically acceptable salt thereof for improving the homogeneity of the complexion and/or for reviving the radiance of the complexion.

The compounds of formula (I) as defined in the present invention or a cosmetically acceptable salts thereof are not, at the present time, known to be used for depigmenting, lightening or even bleaching keratin materials, especially the skin, or for improving the homogeneity of the complexion, or for reviving the radiance of the complexion.

A subject of the invention is also a non-therapeutic cosmetic treatment process for depigmenting, lightening and/or bleaching keratin materials, especially the skin of the face and/or the body, and/or for preventing, reducing and/or treating impairment of the skin complexion or of the colour of the semi-mucous membranes, comprising at least one step consisting in applying, to the skin of the face and/or the body, at least one composition comprising at least one compound of formula (I) as defined in the present invention.

For the purposes of the present invention, the term "preventing" or "prevention" means at least partially reducing the risk of occurrence of a given phenomenon, i.e., in the present invention, impairment of the skin complexion or of the colour of the semi-mucous membranes.

A subject of the invention is also the compounds of formula (I) as defined below for their dermatological use for depigmenting the skin.

For the purposes of the present invention, the term "keratin materials" means human keratin materials, and in particular the skin, bodily hair, the eyelashes, head hair, the lips and the nails of human beings.

The term "skin" means all of the skin of the body, including the scalp, the mucous membranes and the semi-mucous membranes. More particularly, in the present invention, the skin of the neckline, the neck and the face, the hands, the underarms and especially the skin of the face, are considered.

The compounds of formula (I) in accordance with the invention may also make it possible to depigment and/or lighten bodily hair, the eyelashes, head hair, and also the lips and/or the nails.

More particularly, the term "keratin materials" denotes human skin.

One subject of the invention is thus the novel compounds of formula (I) corresponding to formula (I) below:

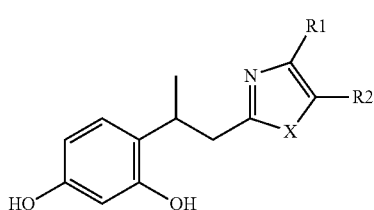

(I)

X denotes an oxygen atom O, a sulfur atom S or a radical $NR_a$ $R_1$ and $R_2$ independently denote:
a hydrogen atom H,
a linear or branched, saturated $C_1$-$C_6$ hydrocarbon-based radical, optionally substituted with one or more hydroxyl radicals,
a linear or branched, unsaturated $C_2$-$C_6$ hydrocarbon-based radical, optionally substituted with one or more hydroxyl radicals, or $R_1$ and $R_2$ may form, together with each carbon atom that bears them, a phenyl group optionally substituted with one or more radicals —$OR_b$, $R_a$ and $R_b$ independently denote:
a hydrogen atom H,
a linear or branched saturated $C_1$-$C_6$ hydrocarbon-based radical, or
an acetyl radical;

and also the salts thereof, the solvates thereof and the optical and/or geometrical isomers thereof, including enantiomers and diastereoisomers, and the racemic mixtures thereof, alone or as a mixture.

In the context of the present invention, the salts of the compounds of formula (I) comprise the conventional non-toxic salts of said compounds such as those formed from acid or base.

As salts of the compound of formula (I), mention may be made of the salts obtained by addition of the compound of formula (I) with a base, which may be organic or mineral. The base may thus be a mineral base, such as sodium hydroxide, potassium hydroxide, calcium hydroxide, ammonium hydroxide, magnesium hydroxide, lithium hydroxide, or sodium, potassium or calcium carbonate or hydrogen carbonate, for example. The base may also be an organic base such as a primary, secondary or tertiary alkylamine, for example triethylamine or butylamine. This primary, secondary or tertiary alkylamine may comprise one or more nitrogen and/or oxygen atoms and may thus comprise, for example, one or more alcohol functions; mention may be made especially of 2-amino-2-methylpropanol, ethanolamine, triethanolamine, 2-dimethylaminopropanol, 2-amino-2-(hydroxymethyl)-1,3-propanediol and 3-(dimethylamino)propylamine.

The salts may also denote salts of addition with amino acids, for instance lysine, arginine or guanidine.

Advantageously, the salts of the compounds of formula (I) may be chosen from alkali metal or alkaline-earth metal salts such as sodium, potassium, calcium or magnesium salts; ammonium salts.

The solvates comprise conventional solvates such as those formed during the preparation of said compounds due to the presence of solvents. Examples that may be mentioned include solvates due to the presence of water or of linear or branched alcohols, such as ethanol or isopropanol.

The optical isomers are especially enantiomers and diastereoisomers.

A "Cx-Cy hydrocarbon-based radical" denotes a radical comprising from x to y carbon atoms. Such a hydrocarbon-based radical may be linear and saturated and typically contain from 1 to 6 carbon atoms or from 1 to 2 carbon atoms such as a methyl or ethyl radical. It may also be linear and unsaturated (ethylenic double bond) and typically contain from 2 to 6 carbon atoms or from 2 to 4 carbon atoms. It may also be branched and typically contain from 3 to 6 carbon atoms or from 3 to 5 carbon atoms.

Unless otherwise indicated, a "Cx-Cy hydrocarbon-based radical" denotes a saturated linear alkyl group comprising from x to y carbon atoms.

Preferentially, the linear saturated or branched hydrocarbon-based radicals are chosen from methyl, ethyl, propyl, isopropyl, butyl, isobutyl, tert-butyl, pentyl and hexyl.

More preferentially, the saturated linear or branched hydrocarbon-based radicals are chosen from methyl, ethyl, propyl, isopropyl, butyl, isobutyl, tert-butyl, pentyl and hexyl, more preferentially from methyl and ethyl, and even more preferentially methyl.

A "Cx-Cy alkyl radical" denotes a saturated Cx-Cy hydrocarbon-based radical. Such a hydrocarbon-based radical may be linear and saturated and typically contain from 1 to 6 carbon atoms or from 1 to 2 carbon atoms such as a methyl or ethyl radical. It may also be branched and typically contain from 3 to 6 carbon atoms or from 3 to 5 carbon atoms. Unless otherwise indicated, a "Cx-Cy alkyl radical" denotes a saturated linear alkyl group comprising from x to y carbon atoms.

The saturated linear or branched $C_1$-$C_6$ hydrocarbon-based radical and the unsaturated linear or branched $C_2$-$C_6$ hydrocarbon-based radical according to the invention may optionally be substituted with one or more hydroxyl radicals, especially with one to three hydroxyl radicals, in particular with one hydroxyl radical.

An "aryl group" denotes an unsaturated or partially unsaturated monocyclic carbocyclic group, containing 6 carbon atoms, which is a phenyl group, and which is optionally substituted with one or more identical or different radicals —$OR_b$ as defined above, especially 1 to 3 radicals —$OR_b$, preferably one radical —$OR_b$ as defined above.

Preferentially, $R_1$ and $R_2$ form, together with each carbon atom that bears them, a phenyl group optionally substituted with one or more identical or different radicals —$OR_b$ as defined above, especially 1 to 3 radicals —$OR_b$, preferably one radical —$OR_b$ as defined above, and more preferentially said phenyl radical is unsubstituted.

In a particularly preferred manner, $R_1$ and $R_2$ form, together with each carbon atom that bears them, an unsubstituted phenyl group.

In one particular embodiment according to the invention, the compounds of formula (I) and also the salts thereof, the solvates thereof and the optical and/or geometrical isomers thereof, including enantiomers and diastereoisomers, and the racemic mixtures thereof, alone or as a mixture, are such that:

X denotes an oxygen atom O, a sulfur atom S or a radical $NR_a$;

$R_1$ and $R_2$ independently denote:

a hydrogen atom H, a linear saturated $C_1$-$C_6$ hydrocarbon-based radical, or $R_1$ and $R_2$ may form, together with each carbon atom that bears them, a phenyl group optionally substituted with one or more radicals —$OR_b$, $R_a$ and $R_b$ independently denote:

a hydrogen atom H, a linear saturated $C_1$-$C_2$ hydrocarbon-based radical, or an acetyl radical.

Preferentially, the compounds of formula (I) and also the salts thereof, the solvates thereof and the optical and/or geometrical isomers thereof, including enantiomers and diastereoisomers, and the racemic mixtures thereof, alone or as a mixture, are such that:

X denotes an oxygen atom O, a sulfur atom S or a radical $NR_a$;

$R_1$ and $R_2$ independently denote:

a hydrogen atom H, a linear saturated $C_1$-$C_4$ hydrocarbon-based radical such as methyl or ethyl, or $R_1$ and $R_2$ may form, together with each carbon atom that bears them, a phenyl group optionally substituted with one or more radicals —$OR_b$, and in particular an unsubstituted phenyl radical.

$R_a$ and $R_b$ independently denote:

a hydrogen atom H, a methyl radical, or an acetyl radical.

Preferably, the compounds of formula (I) and also the salts thereof, the solvates thereof and the optical and/or geometrical isomers thereof, including enantiomers and diastereoisomers, and the racemic mixtures thereof, alone or as a mixture, are such that:

X denotes an oxygen atom O, a sulfur atom S or an NH radical;

$R_1$ and $R_2$ independently denote a hydrogen atom H, or $R_1$ and $R_2$ may form, together with each carbon atom that bears them, a phenyl group.

In a particularly preferred embodiment according to the invention, the compounds of formula (I) and also the salts thereof, the solvates thereof and the optical and/or geometrical isomers thereof, including enantiomers and diastereoisomers, and the racemic mixtures thereof, alone or as a mixture, are such that:

$R_1$ denotes a hydrogen atom H, $R_2$ denotes a hydrogen atom H,

X denotes an oxygen atom O, a sulfur atom S or an NH radical.

In another particularly preferred embodiment according to the invention, the compounds of formula (I) and also the salts thereof, the solvates thereof and the optical and/or geometrical isomers thereof, including enantiomers and diastereoisomers, and the racemic mixtures thereof, alone or as a mixture, are such that:

X denotes an oxygen atom O, a sulfur atom S or an NH radical, $R_1$ and $R_2$ form, together with each carbon atom that bears them, a $C_6$ aryl group.

According to a first preferred variant, the compounds of formula (I) and also the salts thereof, the solvates thereof and the optical and/or geometrical isomers thereof, including enantiomers and diastereoisomers, and the racemic mixtures thereof, alone or as a mixture, are such that $R_1$ and $R_2$ are identical and each denote a hydrogen atom, X, $R_a$ and $R_b$ having the definitions given previously or hereinbelow, in the preferences.

According to this variant, preferably, X denotes an oxygen atom O, a sulfur atom S or an NH radical.

As examples of compounds of formula (I) according to this variant, mention may be made of the compounds A, B and C described hereinbelow, and also the salts and solvates thereof, alone or as a mixture.

According to a second preferred variant, the compounds of formula (I) and also the salts thereof, the solvates thereof and the optical and/or geometrical isomers thereof, including enantiomers and diastereoisomers, and the racemic mixtures thereof, alone or as a mixture, are such that $R_1$ and $R_2$ form, together with each carbon atom that bears them, a phenyl group optionally substituted with one or more radicals —$OR_b$, X, $R_a$ and $R_b$ having the definitions given previously or hereinbelow, in the preferences.

According to this variant, preferably, $R_1$ and $R_2$ form, together with each carbon atom that bears them, a phenyl group that is not substituted with a radical —$OR_b$.

As examples of compounds of formula (I) according to this second variant, mention may be made of the compounds C, D and E described hereinbelow, and also the salts and solvates thereof, alone or as a mixture.

As examples of compounds of formula (I) according to this form of the invention, mention may be made of the compounds A, B, C, D, E and F described hereinbelow, and also the salts and solvates thereof, alone or as a mixture.

Preferably, the compounds of formula (I) of the invention denote compounds B, A and D mentioned in table 1 below, and also the salts and solvates thereof, alone or as a mixture. Even more preferably, the compound of formula (I) of the invention denotes compound D, and also the salts and solvates thereof, alone or as a mixture.

TABLE 1

| Compound No. | Structure | Chemical name |
|---|---|---|
| B | 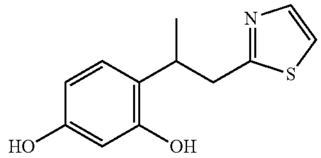 [SMILES: CC(Cc1nccs1)c1ccc(O)cc1O] | 4-[1-(1,3-thiazol-2-yl)propan-2-yl]benzene-1,3-diol |
| F | 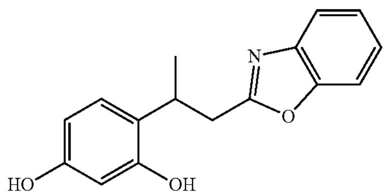 [SMILES: CC(Cc1nc2ccccc2o1)c1ccc(O)cc1O] | 4-[1-(1,3-benzoxazol-2-yl)propan-2-yl]benzene-1,3-diol |
| A | 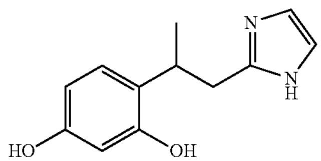 [SMILES: CC(Cc1ncc[nH]1)c1ccc(O)cc1O] | 4-[1-(1H-imidazol-2-yl)propan-2-yl]benzene-1,3-diol |
| C | 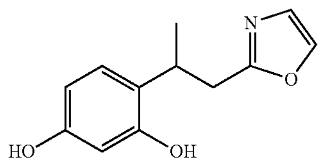 [SMILES: CC(Cc1ncco1)c1ccc(O)cc1O] | 4-[1-(1,3-oxazol-2-yl)propan-2-yl]benzene-1,3-diol |
| D | 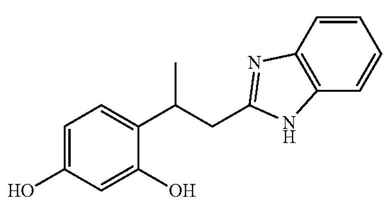 [SMILES: CC(Cc1nc2ccccc2[nH]1)c1ccc(O)cc1O] | 4-[1-(1H-benzimidazol-2-yl)propan-2-yl]benzene-1,3-diol |
| E | | 4-[1-(1,3-benzothiazol-2-yl)propan-2-yl]benzene-1,3-diol | and also the salts and solvates thereof, alone or as a mixture.

The compounds of the invention may be prepared according to schemes 1 and 2 below:

The protection/deprotection steps are those usually used in organic chemistry and compiled in the book "Protecting Groups in Organic Synthesis", Greene, Wuts, Wiley Interscience, depending on the nature of the radicals.

The reactions for forming and reactions involving 5-membered heterocycles are known and described in many literature sources and publications, of which mention may be made of: "Handbook of Heterocyclic Chemistry 3rd Edition", A. R Katritzky, C. A Ramsden, J. A Joule, V. Zhandkin, Elsevier 2010 ISBN 978-0-08-095842-9; "Heterocyclic Chemistry 5th Edition", J. A Joule, K Mills, Wiley ISBN: 978-1-4051-3300-5.

In the schemes that follow, P denotes a protecting group.

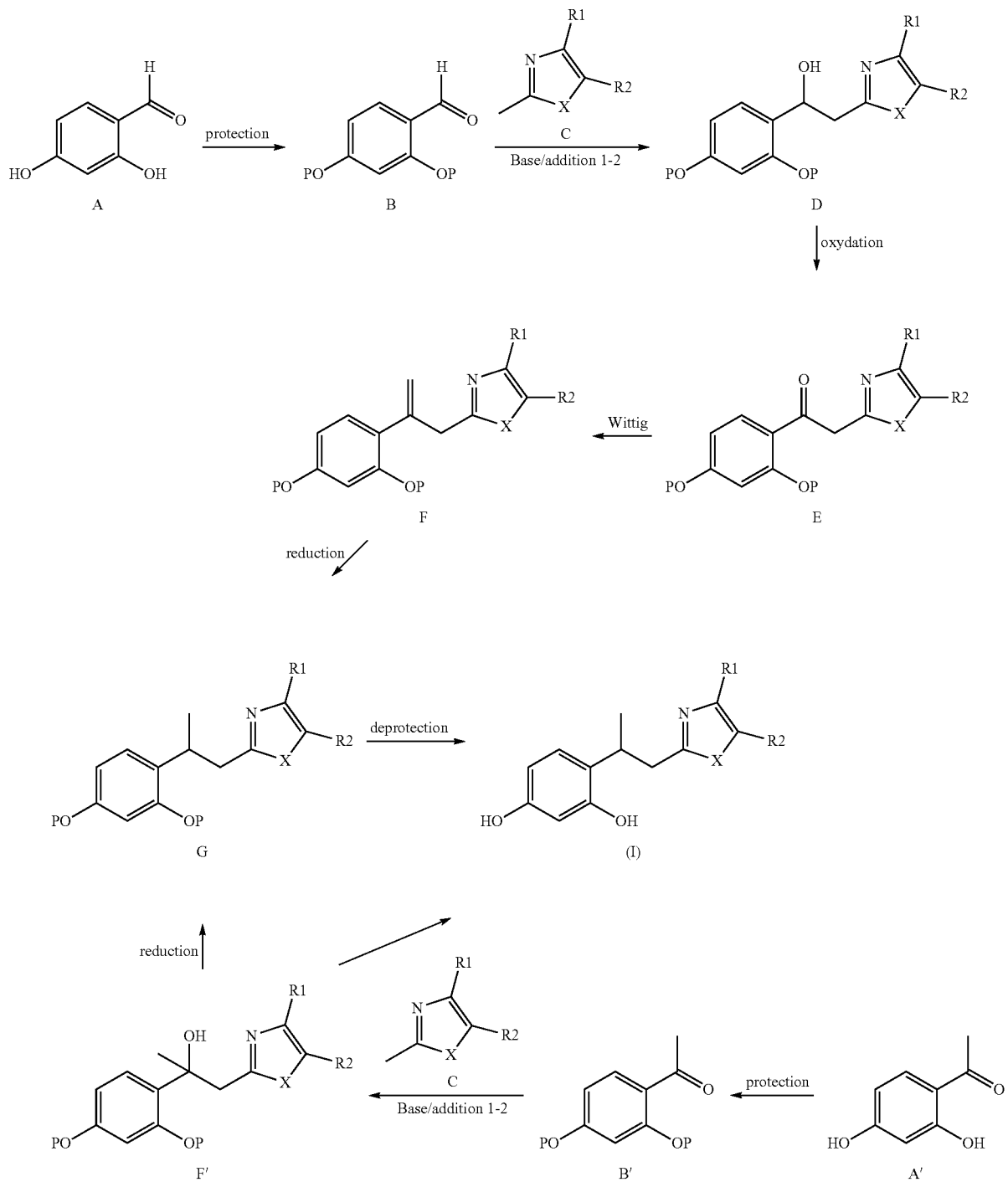

Scheme 1

According to Scheme 1

Aldehyde A or ketone A' are protected on the phenols to give, respectively, compounds B and B'. These compounds are reacted with carbanions obtained by deprotonation of the methyl of the heterocycles C. These deprotonations may be performed in aprotic medium in the presence of a strong base (LDA, LiHMDS, nBuLi) or of alkali metal hydride.

The alcohol function of compounds D or F' thus formed is then either reduced in the case of F' or oxidized in the case of the intermediate D to give the ketone E. E is then subjected to a Wittig or Tebbe olefination reaction to give F.

F and similarly F' are then subjected to a catalytic reduction to give the compounds G, which, after deprotection, lead to the compounds of formula (I).

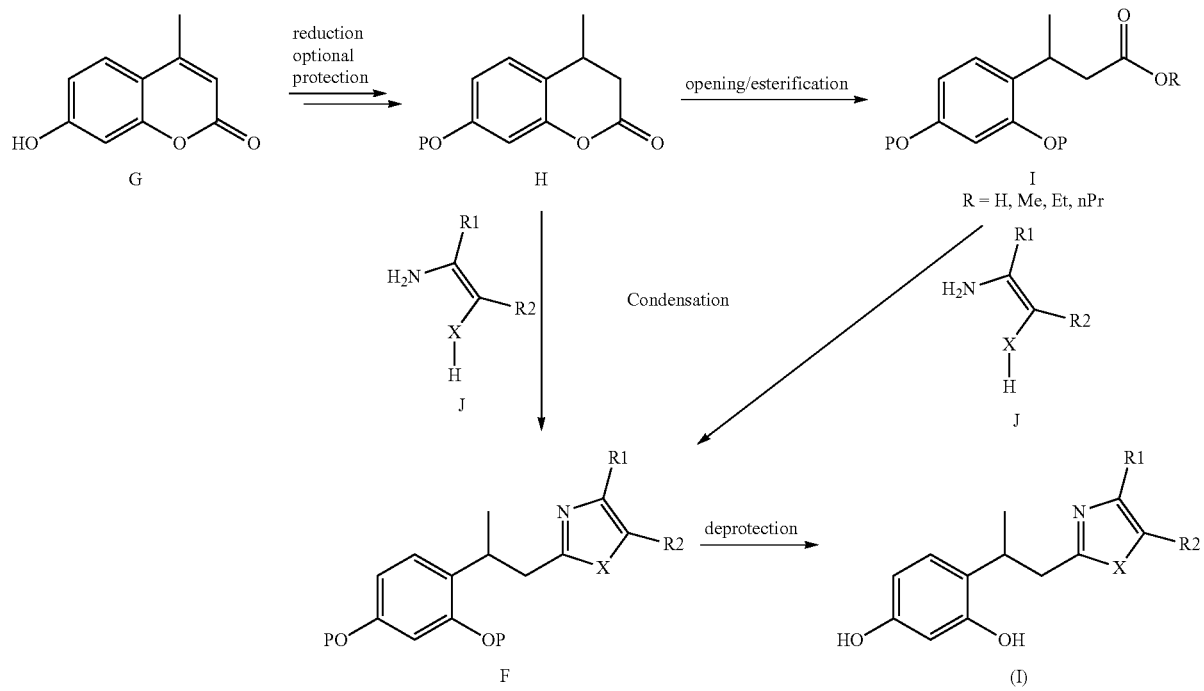

Scheme 2

Scheme 2 illustrates another method for obtaining the compounds (I) from the commercial bicyclic compound G (4-methylumbelliferone CAS 90-33-5) which is reduced to a saturated lactone and optionally protected on the phenolic OH to give compound H.

H may be opened to give the carboxylic derivative (acid or ester) I.

H or I may be subjected to a double condensation via the bis-nucleophile J to give the compounds F, which, after deprotection, lead to the compounds of formula (I).

The compounds of formula (I) according to the invention find a most particular application in the cosmetic field.

A subject of the invention is also a composition containing at least one compound of formula (I), in particular a composition containing at least one compound chosen from compounds A to F described previously, preferably at least one compound chosen from compounds A, B and D, and even more preferentially at least one compound chosen from compound D.

The composition according to the invention is advantageously a cosmetic composition.

The composition according to the invention is advantageously a composition intended for topical application.

The composition according to the invention advantageously comprises, in a physiologically acceptable medium, at least one compound of formula (I) as described previously, in particular at least one compound chosen from compounds A to F described previously, preferably at least one compound chosen from compounds A, B and D, and even more preferentially at least one compound chosen from compound D.

The term "physiologically acceptable medium" means a medium that is compatible with human keratin materials such as the skin, mucous membranes, the nails, the hair, the scalp, or any other area of bodily skin. A physiologically acceptable medium is preferentially a cosmetically acceptable medium, i.e. a medium that is entirely compatible with the route of administration under consideration.

The compound of formula (I) may be present in the composition according to the invention in an amount that may be between 0.01% and 10% by weight, preferably between 0.1% and 5% by weight, especially from 0.5% to 3% by weight relative to the total weight of the composition.

The composition according to the invention is advantageously a cosmetic composition: it may comprise water and/or adjuvants usually used in the cosmetic field.

Mention may be made especially of organic solvents, especially $C_2$-$C_6$ alcohols; oils, especially hydrocarbon-based oils and silicone oils; waxes, pigments, fillers, dyes, surfactants, emulsifiers; cosmetic active agents, organic or mineral photoprotective agents, polymers, thickeners, preserving agents, fragrances, bactericides, ceramides, odour absorbers, antioxidants.

These optional cosmetic adjuvants may be present in the composition in a proportion of from 0.001% to 80% by weight and especially from 0.1% to 40% by weight relative to the total weight of the composition. In any case, these adjuvants, and the proportions thereof, will be chosen by those skilled in the art such that the advantageous properties of the compounds according to the invention are not, or are not substantially, adversely affected by the envisaged addition.

As cosmetic active agents, it will be advantageous to introduce into the composition according to the invention at least one compound chosen from: desquamating agents; calmatives, organic or mineral photoprotective agents, moisturizers; depigmenting agents other than the compounds of the invention; anti-glycation agents; NO-synthase inhibitors; agents for stimulating the synthesis of dermal or epidermal macromolecules and/or for preventing their degradation; agents for stimulating fibroblast and/or keratinocyte proliferation or for stimulating keratinocyte differentiation;

dermo-decontracting agents; tensioning agents; anti-pollution agents and/or free-radical scavengers; agents acting on the microcirculation; agents acting on the energy metabolism of cells; and mixtures thereof.

The composition according to the invention may in particular be in any presentation form normally used in the cosmetic field, and especially in the form of an aqueous or aqueous-alcoholic solution, which is optionally gelled, a dispersion of the lotion type, which is optionally a two-phase lotion, an oil-in-water or water-in-oil or multiple (for example W/O/W or O/W/O) emulsion, an aqueous gel, a dispersion of oil in an aqueous phase by means of spherules, these spherules possibly being polymer nanoparticles such as nanospheres and nanocapsules or, better still, lipid vesicles of the ionic and/or nonionic type; aqueous or oily gels. These compositions are prepared according to the usual methods. The composition according to the invention may constitute a skincare composition, and especially a cleansing, protecting, treating or care cream for the face, the hands, the feet, the major anatomical folds or the body (for example day creams, night creams, makeup-removing creams, foundation creams or antisun creams); a fluid foundation, a makeup-removing milk, a protective or care body milk or an antisun milk; a skincare lotion, gel or foam, such as a cleansing lotion.

A subject of the invention is also a non-therapeutic cosmetic treatment process for depigmenting, lightening and/or bleaching keratin materials, especially the skin of the face and/or the body, and/or for preventing, reducing and/or treating impairment of the skin complexion or of the colour of the semi-mucous membranes, comprising at least one step consisting in applying, to the skin of the face and/or the body, at least one composition comprising at least one compound of formula (I) as defined above in the present invention.

The invention also relates to the non-therapeutic cosmetic use of at least one compound of formula (I) as defined previously, and more particularly at least one compound chosen from compounds A to F described previously, preferably at least one compound chosen from compounds A, B and D, and even more preferentially at least one compound chosen from compound D, as an active agent for depigmenting, lightening and/or bleaching keratin materials, especially the skin of the face and/or of the body, and/or for preventing, reducing and/or treating impairment of the skin complexion or of the colour of the semi-mucous membranes.

The invention is illustrated in greater detail by the following nonlimiting examples.

In the synthetic schemes, "r.t." means room temperature.

EXAMPLE 1: SYNTHESIS OF COMPOUND A

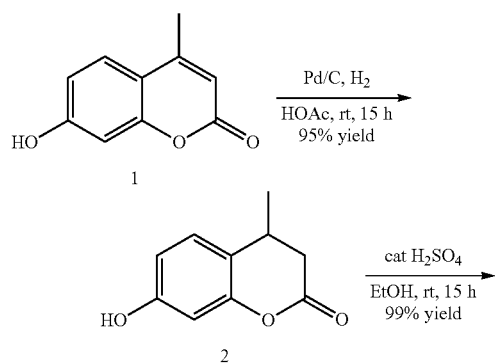

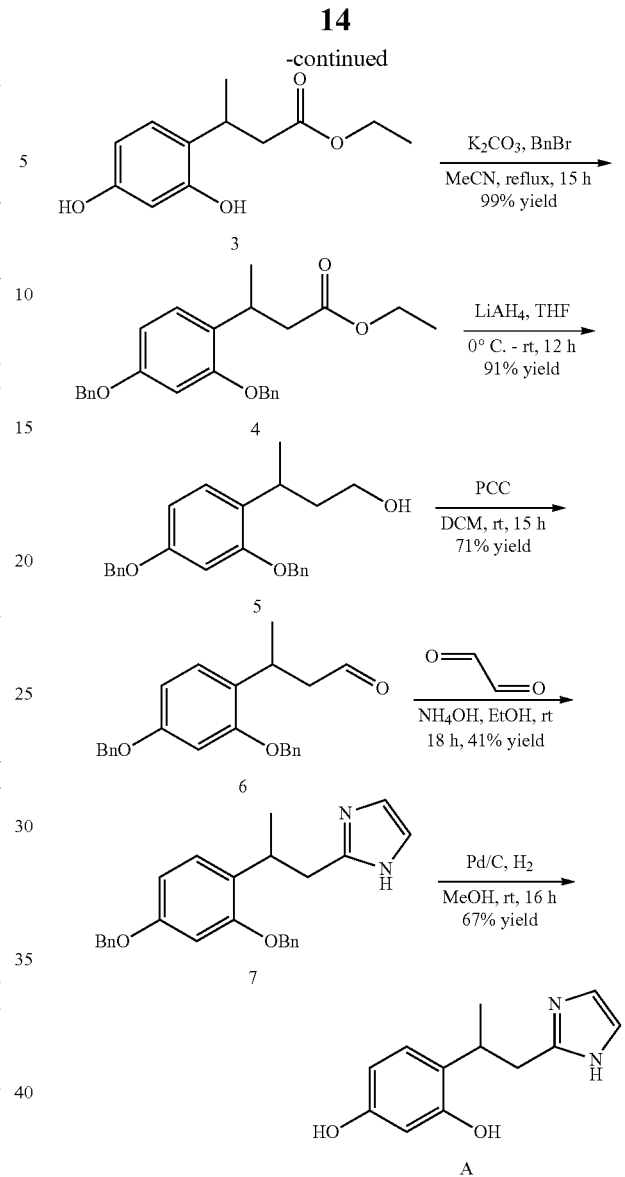

Procedure:

Synthesis of Compound 3: To a solution of compound 2 (5.34 g, 30 mmol) in 80 ml of EtOH is added 1.0 ml of conc. $H_2SO_4$. The mixture is stirred at room temperature for 15 hours. The mixture is then poured into 500 ml of water and extracted three times with EtOAc. The combined organic phases are washed three times with water and concentrated to dryness under vacuum. The crude product is purified by chromatography on a column of silica gel, eluting with 1/1 PE/EtOAc to give 6.65 g of compound 3 in the form of a colourless oil in a yield of 99%.

Synthesis of Compound 4: To a solution of compound 3 (6.4 g, 28.6 mmol) in 80 ml of MeCN are added $K_2CO_3$ (9.8 g, 71.0 mmol) and BnBr (12.14 g, 71.0 mmol). The reaction mixture is refluxed for 15 hours. The mixture is then filtered to remove the salt. The filtrate is concentrated to dryness. The crude product is then purified by chromatography on a column of silica gel, eluting with 5/1 PE/EtOAc to give 11.55 g of compound 4 in the form of a colourless oil in a yield of 100%.

Synthesis of Compound 5: To a suspension of $LiAlH_4$ (3.3 g, 54 mmol) in 80 ml of THF is added compound 4 (11.0 g, 27.2 mmol) in 20 ml of THF. The mixture is stirred at room temperature for 12 hours. 4.0 ml of saturated aqueous Na2SO4 are then added dropwise to the mixture. The mixture is filtered to remove the solids. The filtrate is concentrated to dryness under vacuum. The crude product is then purified by chromatography on a column of silica gel, eluting with 4/1 PE/EtOAc to give 8.96 g of compound 5 in the form of a colourless oil in a yield of 91%.

Synthesis of Compound 6: To a solution of compound 5 (12.5 g, 34.6 mmol) in 120 ml dichloromethane is added PCC (9.7 g, 45 mmol). The mixture is stirred at room temperature for 15 hours and 120 ml of water are added to the mixture, which is extracted with dichloromethane. The organic phases are dried over sodium sulfate and filtered. The filtrate is concentrated under reduced pressure. The resulting residue is purified by chromatography on silica gel (eluent: 1/10 EtOAc/PE) to give 8.9 g of compound 6 in the form of a white solid in a yield of 71%.

Synthesis of Compound 7: To a solution of compound 6 (360 mg, 1 mmol) in 2 ml of ethanol are added 40% oxaldehyde (2 ml) and a 25% solution of $NH_4OH$ (2 ml). The mixture is stirred at room temperature for 18 hours. 30 ml of 2N HCl are then added dropwise and the medium is extracted with ethyl acetate. The combined organic phases are dried over sodium sulfate and filtered. The filtrate is concentrated under reduced pressure. The resulting residue is purified by chromatography on silica gel (eluent: 1/5 EtOAc/PE) to give 163 mg of compound 7 in the form of a white solid in a yield of 41%.

Synthesis of Compound A: To a solution of compound 7 (163 mg, 0.41 mmol) in 5 ml methanol is added Pd/C (20 mg). The mixture is stirred at room temperature for 16 hours under $H_2$. The mixture is then filtered. The filtrate is concentrated under reduced pressure. The resulting residue is purified by chromatography on silica gel (eluent: 1/1 EtOAc/PE) to give 60 mg of compound A in the form of a red solid in a yield of 67%.

The MS and NMR spectra are in accordance with the desired product.

EXAMPLE 2: SYNTHESIS OF COMPOUND B

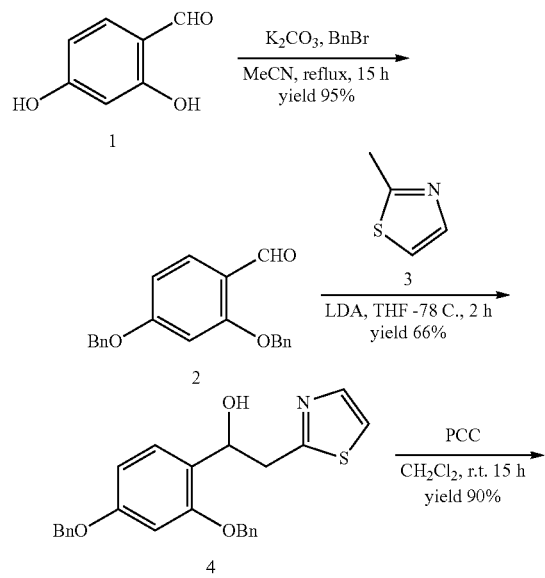

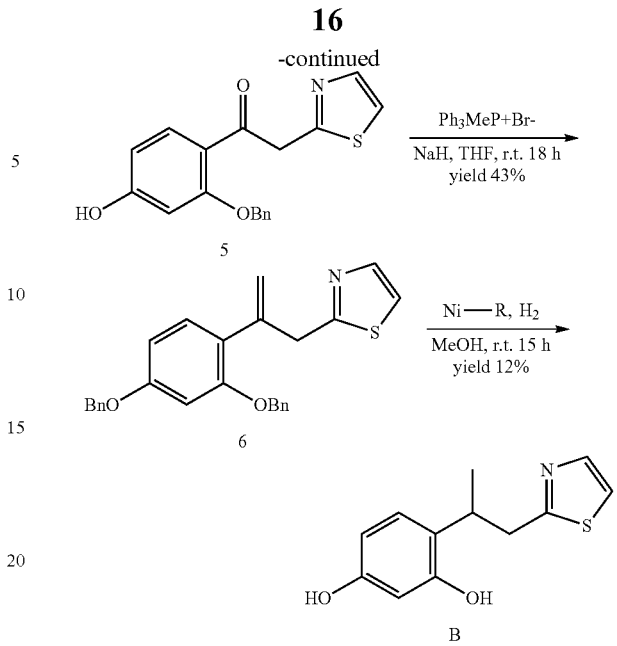

Synthesis of Compound 2: To a solution of compound 1 (3.0 g, 20.0 mmol) in 120 ml of MeCN are added $K_2CO_3$ (13.8 g, 100.0 mmol) and BnBr (15.05 g, 88.0 mmol). The reaction mixture is refluxed for 15 hours. After cooling to room temperature, the mixture is filtered and the filtrate is concentrated to dryness. The resulting residue is purified by chromatography on a column of silica gel using dichloromethane, to give 12.1 g of compound 2 in the form of a white powder in a yield of 95%.

Synthesis of Compound 4: To a solution of compound 3 (1.98 g, 20.0 mmol) in 60 ml of THF are added 10.0 ml of 2.0 M LDA in THF at −78° C. After stirring for 30 minutes, a solution of compound 2 (6.36 g, 20.0 mmol) in 30 ml of THF is added. The reaction mixture is gradually warmed to room temperature and stirred for 2 hours. The reaction is quenched by adding 400 ml of saturated $NH_4Cl$ and extracted three times with EtOAc. The combined organic phases are washed with water and then concentrated to dryness under vacuum. The crude product is then purified by chromatography on a column of silica gel, eluting with 5/1 PE/EtOAc to give 5.5 g of compound 4 in the form of a white solid in a yield of 66%.

Synthesis of Compound 5: To a solution of compound 4 (4.17 g, 10.0 mmol) in 80 ml $CH_2Cl_2$ is added PCC (2.6 g, 12.1 mmol). The reaction medium is stirred at room temperature for 15 hours and then concentrated to dryness under vacuum. The crude product is then purified by chromatography on a column of silica gel, eluting with 5/1 PE/EtOAc to give 3.7 g of compound 5 in the form of a white solid in a yield of 90%.

Synthesis of Compound 6: To a solution of compound 5 (1.15 g, 2.77 mmol) and methyltriphenylphosphonium bromide (1.3 g, 3.6 mmol) in 40 ml THF is added NaH (250 mg, 4.2 mmol). The reaction medium is stirred at room temperature for 18 hours. 200 ml of saturated aqueous $NH_4Cl$ are poured into the mixture and the medium is extracted twice with EtOAc. The combined organic phases are washed with water three times and concentrated to dryness. The resulting residue is purified by chromatography on silica gel (5/1 PE/EtOAc) to give 0.78 g of compound 6 in the form of a yellow oil in a yield of 68%.

Synthesis of Compound B: A mixture of compound 6 (0.78 g, 1.88 mmol) and Ni—R in 30 ml of MeOH is stirred under a hydrogen atmosphere at room temperature for 15 hours. The reaction medium is filtered cautiously and the filtrate is concentrated to dryness. The resulting residue is purified by chromatography on silica gel (250/1 dichloromethane/methanol) to give 54 mg of compound B in the form of a pink powder in a yield of 12%. m.p.: 105-107° C.

The MS and NMR spectra are in accordance with the desired product.

EXAMPLE 3: SYNTHESIS OF COMPOUND C

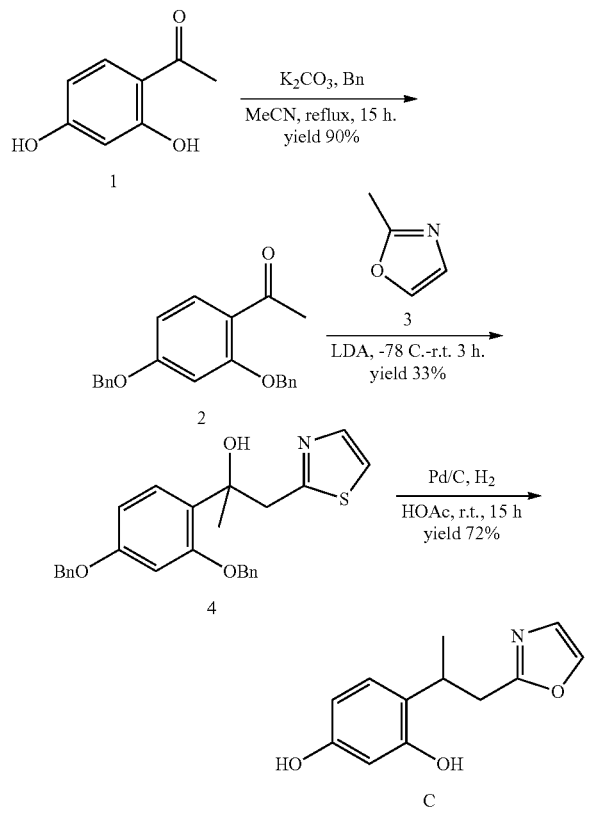

Synthesis of Compound 2: To a solution of compound 1 (3.0 g, 20.0 mmol) in 120 ml of MeCN are added $K_2CO_3$ (13.8 g, 100.0 mmol) and BnBr (8.55 g, 50.0 mmol). The reaction mixture is refluxed for 15 hours. After cooling to room temperature, the mixture is filtered and the filtrate is concentrated to dryness. The resulting residue is purified by chromatography on a column of silica gel using dichloromethane, to give 6.0 g of compound 2 in the form of a white powder in a yield of 90%.

Synthesis of Compound 4: To a solution of compound 3 (0.83 g, 10.0 mmol) in 50 ml of THF are added 5.0 ml of 2.0 M LDA in THF at −78° C. After stirring for 30 minutes, a solution of compound 2 (3.0 g, 10.0 mmol) in 30 ml of THF is added. The reaction medium is gradually warmed to room temperature and stirred for 2 hours. The reaction is quenched by adding 400 ml of saturated $NH_4Cl$ and the medium is extracted three times with EtOAc. The combined organic phases are washed with water and then concentrated to dryness under vacuum. The crude product is then purified by chromatography on a column of silica gel, eluting with 5/1 PE/EtOAc to give 1.37 g of compound 4 in the form of a white solid in a yield of 33%.

Synthesis of Compound C: A mixture of compound 4 (1.34 g, 3.2 mmol) and 10% Pd/C in 40 ml of AcOH is stirred under a hydrogen atmosphere at room temperature for 15 hours. The reaction medium is filtered and the filtrate is concentrated to dryness. The resulting residue is purified by chromatography on silica gel (500/5 dichloromethane/methanol) to give 500 mg of compound C in the form of a white powder in a yield of 72%. m.p.: 100-102° C.

The MS and NMR spectra are in accordance with the desired product.

EXAMPLE 4: SYNTHESIS OF COMPOUND D

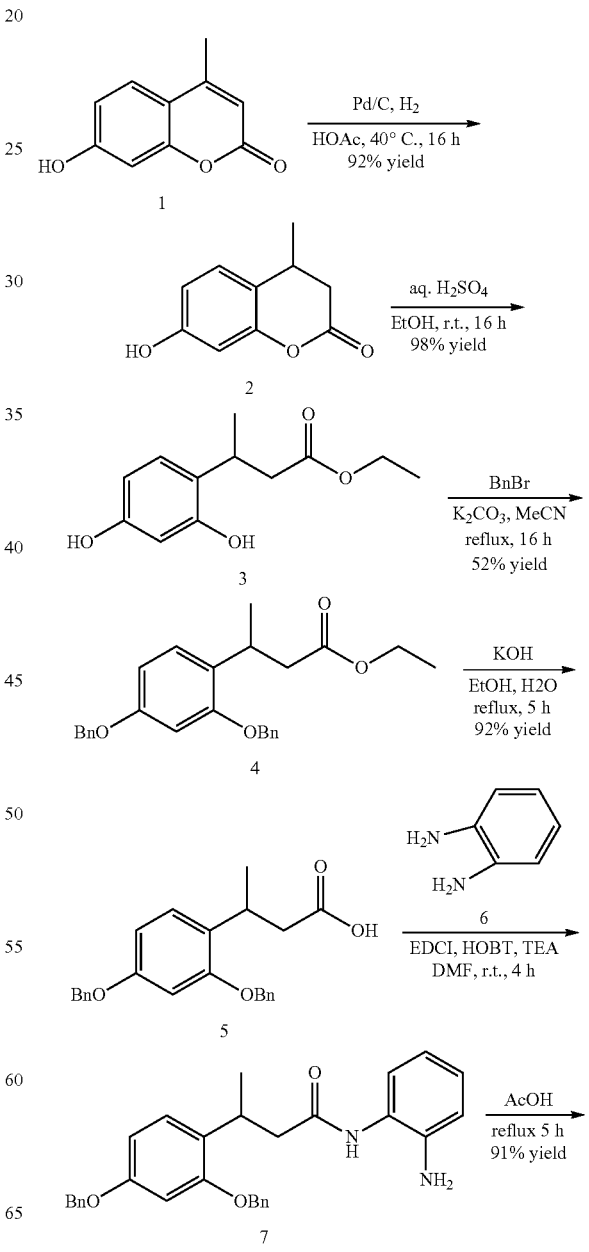

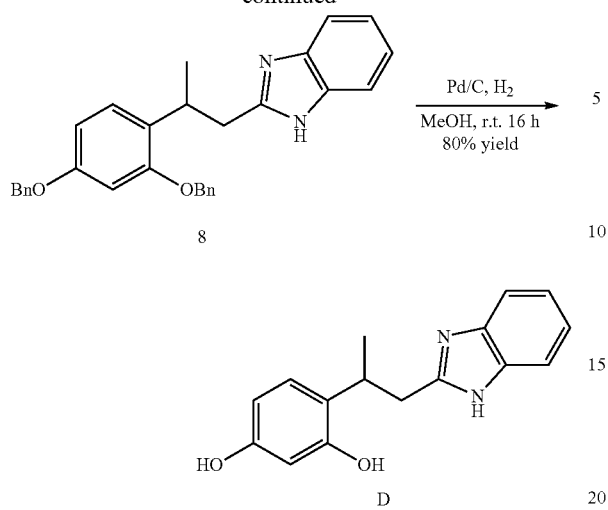

8

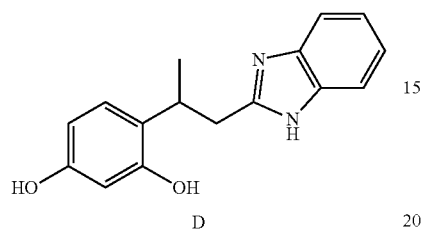

D

The synthesis of compound 4 is described in the synthesis of Example 1.

Synthesis of Compound 5: To a solution of compound 4 (2.43 g, 6.0 mmol) in 50 ml of ethanol is added a solution of KOH (673 mg, 12 mmol) in 5 ml of water. The mixture is refluxed for 5 hours. After cooling the mixture, 30 ml of 2N HCl are added and the medium is extracted with ethyl acetate. The combined organic phases are dried over sodium sulfate and filtered. The filtrate is concentrated under reduced pressure to give 2.07 g of compound 5 in the form of a white solid in a yield of 92%.

Synthesis of Compound 7: To a solution of compound 5 (350 mg, 0.93 mmol) in 10 ml of DMF are added benzene-1,2-diamine (119 mg, 1.1 mmol), EDCI (210 mg, 1.1 mmol), HOBT (149 mg, 1.1 mmol) and triethylamine (111 mg, 1.1 mmol). The mixture is stirred at room temperature for 4 hours and then poured into 50 ml of water and extracted with ethyl acetate. The combined organic phases are dried over sodium sulfate, filtered and concentrated under reduced pressure. The resulting residue is purified by chromatography on silica gel (eluent: 1/2 EtOAc/PE) to give 320 mg of compound 7 in the form of a white solid in a yield of 74%.

Synthesis of Compound 8: Compound 7 (93 mg, 0.2 mmol) in 10 ml of acetic acid is refluxed for 5 hours. After cooling the mixture, the solvent is removed under reduced pressure. The resulting residue is purified by chromatography on silica gel (eluent: 1/2 EtOAc/PE) to give 82 mg of compound 8 in the form of a white solid in a yield of 91%.

Synthesis of Compound D: To a solution of compound 8 (82 mg, 0.18 mmol) in 20 ml methanol is added Pd/C (25 mg). The mixture is stirred at room temperature for 16 hours under $H_2$. The mixture is then filtered. The filtrate is concentrated under reduced pressure. The resulting residue is purified by chromatography on silica gel (eluent: 1/1 EtOAc/PE) to give 39 mg of compound D in the form of a white solid in a yield of 80%.

The MS and NMR spectra are in accordance with the desired product.

EXAMPLE 5: SYNTHESIS OF COMPOUND E

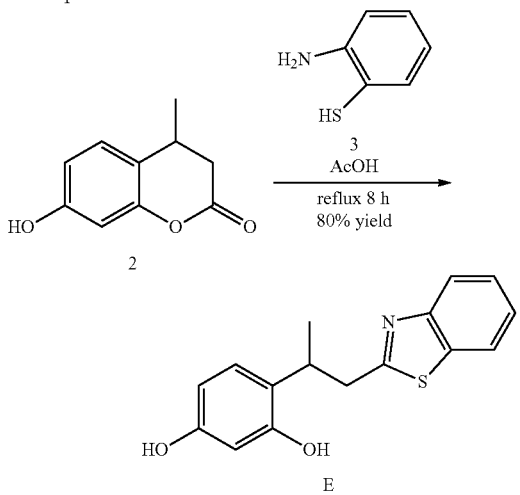

The synthesis of 2 is described above in Example 4.

Synthesis of Compound E: A mixture of compound 2 (534 mg, 3.0 mmol) and of compound 3 (563 mg, 4.5 mmol) in 25 ml of AcOH is refluxed for 8 hours. The reaction medium is cooled to room temperature and then poured into 200 ml of water and extracted three times with EtOAc. The combined organic phases are washed three times with water and concentrated to dryness under vacuum. The crude product is then purified by chromatography on a column of silica gel, eluting with 50/1 $CH_2Cl_2$/MeOH to give 684 mg of compound E in the form of a white solid in a yield of 80%. m.p.: 98-100° C.

The MS and NMR spectra are in accordance with the desired product.

EXAMPLE 6: SYNTHESIS OF COMPOUND F

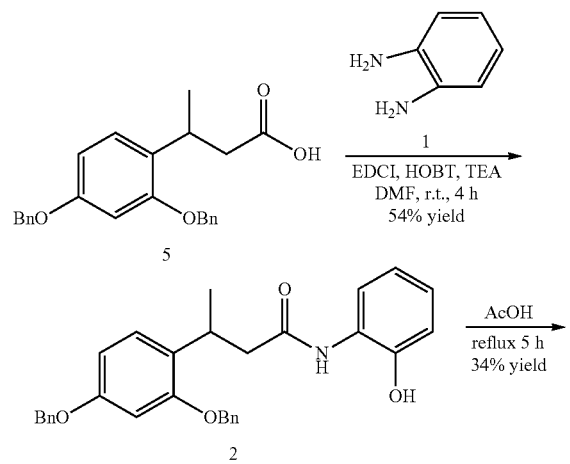

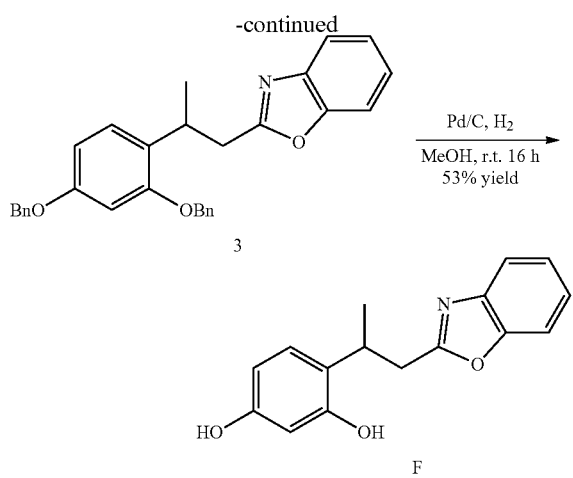

The synthesis of compound 5 is described in the synthesis of compound D described in Example 4.

Synthesis of Compound 2: To a solution of compound 5 (753 mg, 2 mmol) in 10 ml of DMF are added 2-aminophenol 1 (262 mg, 2.4 mmol), EDCI (458 mg, 2.4 mmol), HOBT (324 mg, 2.4 mmol) and triethylamine (242 mg, 2.4 mmol). The mixture is stirred at room temperature for 4 hours and then poured into 50 ml of water and extracted with ethyl acetate. The combined organic phases are dried over sodium sulfate and filtered. The filtrate is concentrated under reduced pressure. The resulting residue is purified by chromatography on silica gel (eluent: 1/2 EtOAc/PE) to give 505 mg of compound 2 in the form of a white solid in a yield of 54%.

Synthesis of compound 3: Compound 2 (504 mg, 1.08 mmol) in 10 ml of acetic acid is refluxed for 5 hours. After cooling the mixture, the solvent is removed under reduced pressure. The resulting residue is purified by chromatography on silica gel (eluent: 1/2 EtOAc/PE) to give 168 mg of compound 3 in the form of a white solid in a yield of 34%.

Synthesis of compound F: To a solution of compound 3 (166 mg, 0.37 mmol) in 20 ml methanol is added Pd/C (20 mg). The mixture is stirred at room temperature for 16 hours under $H_2$. The mixture is then filtered. The filtrate is concentrated under reduced pressure. The resulting residue is purified by chromatography on silica gel (eluent: 1/1 EtOAc/PE) to give 460 mg of compound F in the form of a white solid in a yield of 53%.

The MS and NMR spectra are in accordance with the desired product.

EXAMPLE 7: DEMONSTRATION OF THE DEPIGMENTING ACTIVITY

The measurement of the depigmenting activity (reduction of melanin production) of compounds of formula (I) was performed by assaying normal human melanocytes in vitro as follows.

First, normal human melanocytes are cultured and distributed in a multiwell plate. After 24 hours, the culture medium was replaced with a medium containing the compounds of formula (I) to be evaluated. The cells were incubated 72 hours before measurement of the final optical density, which measures the amount of melanin produced by the melanocytes. A dose effect was performed using a wide concentration range of the compounds evaluated. Thus, by making the concentrations and the melanin measurements correspond, it was possible to determine an IC50 in μM: concentration at which a 50% decrease in melanin synthesis is achieved.

Various test campaigns were conducted and the test results are collated in the tables below.

These results were compared with those obtained with compounds described in the prior art, and more particularly the compound 5-[(E)-2-(4-hydroxyphenyl)ethenyl]benzene-1,3-diol described in patent application JP01038009A.

| Compound No. | Structure | IC50 (μM) | Maximum concentration tested (μM) |
|---|---|---|---|
| Compound B | | 5.9 | 200 |
| Compound D | 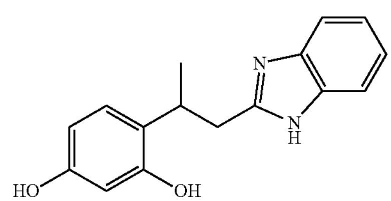 [SMILES: CC(Cc1nc2ccccc2[nH]1)c1ccc(O)cc1O] | 3.7 | 200 |
| Compound of the prior art | Reference 5-[(E)-2-(4-hydroxyyphenyl)ethenyl]benzene-1,3-diol | 8.18 | 200 |
| Compound B | | 1.07* | 200 |

-continued

| Compound No. | Structure | IC50 (µM) | Maximum concentration tested (µM) |
|---|---|---|---|
| Compound A | 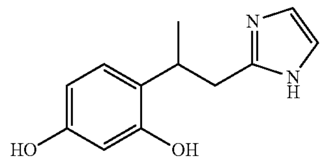 [SMILES: CC(Cc1ncc[nH]1)c1ccc(O)cc1O] | 3.7* | 200 |
| Compound D | 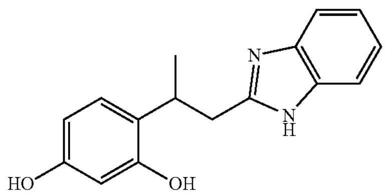 [SMILES: CC(Cc1nc2ccccc2[nH]1)c1ccc(O)cc1O] | 6.7* | 200 |

*Different campaigns each time

The compounds of formula (I) showed a strong depigmenting effect.

Coculture Experiment:

A biological test demonstrated the depigmenting activity of compound D.

The melanogenesis-modulating effect of compound D was measured according to the method described in patent FR-A-2734825, and also in the article by R. Schmidt, P. Krien and M. Régnier, Anal. Biochem., 235(2), 113-18, 1996. This test is performed on a coculture of keratinocytes and melanocytes.

For the test compounds, the following were determined:
the cytotoxicity,
the inhibitory activity on melanin synthesis, by estimating the melanin optical density.

The IC50 values (concentration for which 50% of the melanin synthesis is inhibited) were determined.

5-[(E)-2-(4-hydroxyphenyl)ethenyl]benzene-1,3-diol described in patent application JP01038009 A The test was also performed with the compound 5-[(E)-2-(4-hydroxyphenyl)ethenyl]benzene-1,3-diol described in the prior art patent application JP01038009, Prior art compound 5-[(E)-2-(4-hydroxyphenyl)ethenyl] benzene-1,3-diol: Non-cytotoxic, IC 50=2.77 µM Compound D: non-cytotoxic, IC50=1.38 µM

EXAMPLE 8: COSMETIC COMPOSITION

A skin depigmenting composition is prepared, comprising (in grams):

| | | |
|---|---|---|
| Compound D | 2 g |
| PEG400 | 68 g |
| Ethanol | 30 g |

The composition applied to the skin makes it possible to homogenize the complexion and especially to attenuate brown spots.

EXAMPLE 9: GEL

A skin depigmenting gel is prepared, comprising (% by weight):

| | | |
|---|---|---|
| Compound D | 0.5% |
| Carbomer (Carbopol 981 from Lubrizol) | 1% |
| Preserving agent | qs |
| Water | qs 100% |

The composition applied to the skin makes it possible to attenuate and homogenize the complexion and brown spots.

The invention claimed is:
1. A compound of formula (I):

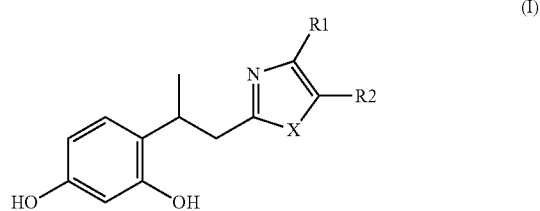

wherein:
X denotes an oxygen atom O, a sulfur atom S or a radical NR$_a$;
R$_1$ and R$_2$ independently denote:
a hydrogen atom H,
a linear or branched, saturated C$_1$-C$_6$ hydrocarbon-based radical, optionally substituted with one or more hydroxyl radicals,
a linear or branched, unsaturated C$_2$-C$_6$ hydrocarbon-based radical, optionally substituted with one or more hydroxyl radicals, or
R$_1$ and R$_2$ form, together with each carbon atom that bears them, a phenyl group optionally substituted with one or more radicals —OR$_b$,
R$_a$ and R$_b$ independently denote:
a hydrogen atom H,
a linear or branched saturated C$_1$-C$_6$ hydrocarbon-based radical, or
an acetyl radical;
and also the salts thereof, the solvates thereof and the optical and/or geometrical isomers thereof, including enantiomers and diastereoisomers, and the racemic mixtures thereof, alone or as a mixture, with the proviso that the compound is not 4-[1-(1H-imidazol-2-yl)propan-2-yl]benzene-1,3-diol:

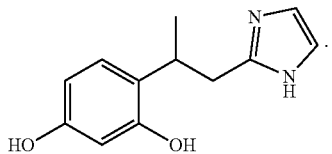 [SMILES: CC(Cc1ncc[nH]1)c1ccc(O)cc1O]

2. The compound according to claim 1, wherein:
X denotes an oxygen atom O, a sulfur atom S or a radical $NR_a$;
$R_1$ and $R_2$ independently denote:
a hydrogen atom H,
a linear saturated $C_1$-$C_6$ hydrocarbon-based radical, or
$R_1$ and $R_2$ form, together with each carbon atom that bears them, a phenyl group optionally substituted with one or more radicals —$OR_b$,
$R_a$ and $R_b$ independently denote:
a hydrogen atom H,
a linear saturated $C_1$-$C_2$ hydrocarbon-based radical, or
an acetyl radical.

3. The compound according to claim 1, wherein:
X denotes an oxygen atom O, a sulfur atom S or a radical $NR_a$;
$R_1$ and $R_2$ independently denote:
a hydrogen atom H,
a linear saturated $C_1$-$C_2$ hydrocarbon-based radical, or
$R_1$ and $R_2$ form, together with each carbon atom that bears them, a phenyl group optionally substituted with one or more radicals —$OR_b$,
$R_a$ and $R_b$ independently denote:
a hydrogen atom H,
a methyl radical, or
an acetyl radical.

4. The compound according to claim 1, wherein:
X denotes an oxygen atom O, a sulfur atom S or a radical $NR_a$;
$R_1$ and $R_2$ independently denote:
a hydrogen atom H, or
$R_1$ and $R_2$ form, together with each carbon atom that bears them, a phenyl group,
$R_a$ denotes a hydrogen atom H.

5. The compound according to claim 1, selected from the group consisting of:

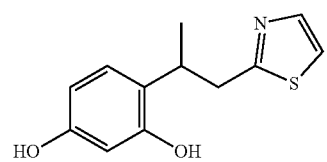 [SMILES: CC(Cc1nccs1)c1ccc(O)cc1O]

4-[1-(1,3-thiazol-2-yl)propan-2-yl]benzene-1,3-diol;

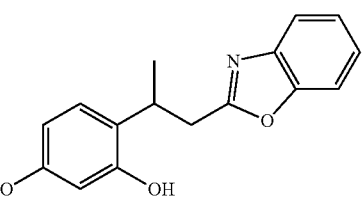

4-[1-(1,3-benzoxazol-2-yl)propan-2-yl]benzene-1,3

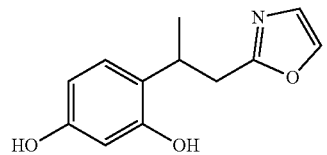 [SMILES: CC(Cc1ncco1)c1ccc(O)cc1O]

4-[1-(1,3-oxazol-2-yl)propan-2-yl]benzene-1,3-diol;

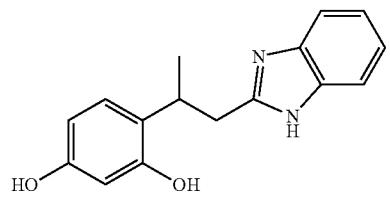 [SMILES: CC(Cc1nc2ccccc2[nH]1)c1ccc(O)cc1O]

4-[1-(1H-benzimidazol-2-yl)propan-2-yl]benzene-1,3-diol;

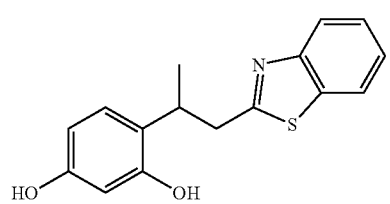 [SMILES: CC(Cc1nc2ccccc2s1)c1ccc(O)cc1O]

4-[1-(1H-benzimidazol-2-yl)propan-2-yl]benzene-1,3-diol,
and also the salts thereof, the solvates thereof and/or the optical isomers thereof, including enantiomers and diastereoisomers, and the racemic mixtures thereof, alone or as a mixture.

6. A composition comprising, in a physiologically acceptable medium, at least one compound of formula (I) according to claim 1.

7. The composition according to claim 6, wherein compound of formula (I) is present in a content of between 0.01% and 10% by weight relative to the total weight of the composition.

8. The composition according to claim 6, further comprising: at least one adjuvant selected from the group consisting of organic solvents, oils, waxes, pigments, fillers, dyes, surfactants, emulsifiers; cosmetic active agents, organic or mineral photoprotective agents, polymers, thickeners, preserving agents, fragrances, bactericides, ceramides, odour absorbers and antioxidants.

9. The composition according to claim 6 further comprising at least one active agent selected from the group consisting of desquamating agents; calmatives, organic or mineral photoprotective agents, moisturizers; depigmenting agents other than the compounds of the invention; antiglycation agents; NO-synthase inhibitors; agents for stimulating the synthesis of dermal or epidermal macromolecules and/or for preventing their degradation; agents for stimulating fibroblast and/or keratinocyte proliferation or for stimulating keratinocyte differentiation; tensioning agents; antipollution agents and/or free-radical scavengers; agents acting on microcirculation; agents acting on energy metabolism of cells; and mixtures thereof.

10. A non-therapeutic cosmetic process for depigmenting, lightening and/or bleaching keratin materials, and/or for reducing and/or treating impairment of skin complexion or of colour of semi-mucous membranes, comprising: applying, to the skin of a face and/or body, at least one composition comprising at least one compound of formula (I) as defined according to claim 1.

11. The process according to claim 10 for depigmenting, lightening and/or bleaching the skin.

12. A method for depigmenting, lightening and/or bleaching keratin materials, and/or for reducing and/or treating impairment of skin complexion or of colour of semi-mucous membranes comprising applying the composition of claim 6 to the keratin material, skin or semi-mucous membrane.

13. The method according to claim 12, for making the complexion homogeneous and/or reviving the radiance of the complexion.

\* \* \* \* \*

UNITED STATES PATENT AND TRADEMARK OFFICE
CERTIFICATE OF CORRECTION

PATENT NO. : 11,389,385 B2
APPLICATION NO. : 16/650645
DATED : July 19, 2022
INVENTOR(S) : Marat et al.

It is certified that error appears in the above-identified patent and that said Letters Patent is hereby corrected as shown below:

In the Claims

In Column 24, Claim 1, Line 59, delete "$R_h$" and insert -- $R_b$ --.

In Column 25, Claim 2, Line 21, delete "$R_h$" and insert -- $R_b$ --; and

In Column 25, Claim 5, Line 67, delete "1,3" and insert -- 1,3-diol; --.

Signed and Sealed this
Twenty-second Day of November, 2022

*Katherine Kelly Vidal*

Katherine Kelly Vidal
*Director of the United States Patent and Trademark Office*